(12) United States Patent
Ahmed et al.

(10) Patent No.: US 7,528,128 B2
(45) Date of Patent: May 5, 2009

(54) PYRROLO[2,1-C][1,4]BENZODIAZEPINE HYBRIDS AND A PROCESS FOR THE PREPARATION THEREOF

(75) Inventors: Kamal Ahmed, Andhra Pradesh (IN); Rajendra Prasad Bandari, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 11/893,101

(22) Filed: Aug. 13, 2007

(65) Prior Publication Data

US 2008/0064870 A1 Mar. 13, 2008

(30) Foreign Application Priority Data

Aug. 14, 2006 (IN) .................. 1823/DEL/2006

(51) Int. Cl.
*C07D 243/14* (2006.01)
*A61K 31/5517* (2006.01)

(52) U.S. Cl. ....................... 514/220; 540/496
(58) Field of Classification Search ................. 540/496; 514/220
See application file for complete search history.

(56) References Cited

OTHER PUBLICATIONS

Gregson et al., "Design, synthesis and evaluation of a novel pyrrolobenzodiaepine DNA-interactive agent with highly efficient cross-linking ability and potent cytotoxicity", *Journal of Medicinal Chemistry* 44(5):737-48 (2001).
Hurley et al., "Pyrrolo(1,4) benzodiazepine antitumor antibiotics. In vitro interaction of anthramycin sibiromycin and tomaymycin with DNA using specifically radiolabelled molecules", *Biochimica et biophysica acta* 475(3):521-35 (1977).
Kamal et al., Design, synthesis and evaluation of new noncrosslinking pyrrolobenzodiazepine dimers with efficient DNA binding ability and potent antitumor activity, *Journal of Medicinal Chemistry* 45(21):4679-88 (2002).
Kamal et al., "Synthesis of novel C2 and C2-C8 linked pyrrolo[2,1-c] [1,4] benzodiazepine-naphthalimide mybrids as DNA-binding agents", *Bioorganic & Medicinal Chemistry Letters* 13(20):3577-81 (2003).
Kaplan et al., " Anthramycin binding to deoxyribonucleic acid-mitomycin C complexes. Evidence for drug-induced deoxyribonucleic acid conformational change and cooperativity in mitomycin C binding", *Biochemistry* 20(26):7572-80 (1981).
Kohn et al., "Reaction of anthramycin with deoxyribonucleic acid", *Journal of Molecular Biology* 51(3):551-72 (1970).
Kunimoto et al., "Mazehtramycin, a new member of anthramycin group antibiotics", *Journal of Antibiotics* 33(6)665-7 (1980).
Liou et al., "Synthesis and structure-activity relationship of 2-aminobenzophenone derivatives as antimitotic agents", *Journal of Medicinal Chemistry* 45(12):2556-2562 (2002).
Thurston et al., Synthesis of a novel GC-specific covalent-binding DNA affinity-cleavage agent based on pyrrolobenzodiazepines (PBDs), *Chemical Communications* 563-565 (1996).
Thurston et al., "Synthesis of Sequence-Selective C8-Linked Pyrrolo[2,1-c] [1,4] benzodiazepine DNA Interstrand Cross-Linking Agents", *Journal of Organic Chemistry* 61(23):8141-8147 (1996).

*Primary Examiner*—Bruck Kifle
(74) *Attorney, Agent, or Firm*—DLA Piper LLP (US)

(57) ABSTRACT

The present invention provides a compound of general formula 5, useful as potential antitumour agents against human cancer cell lines. The present invention further provides a process for the preparation of pyrrolo[2,1-c][1,4]benzodiazepine hybrids of general formula 5

Formula 5

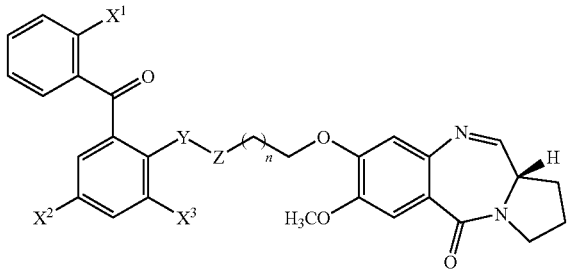

$X^1, X^2, X^3$ = H (or) Cl (or) $CH_3$
Y = O (or) NH
Z = C=O (or) $CH_2$ wherein, X1, X2, X3 is selected from H or Cl or CH3, Y is selected from O or NH, Z is selected from C=O or CH2 and n=1 to 4.

11 Claims, 1 Drawing Sheet

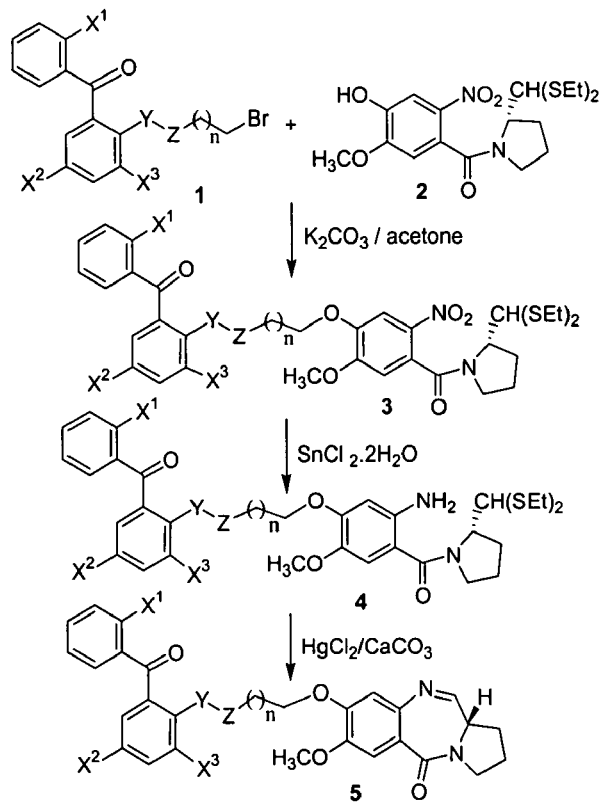
| Compound | x¹ | x² | x³ | Y | Z | n |
|---|---|---|---|---|---|---|
| 5a | H | Cl | H | O | CH₂ | 1 |
| 5b | H | Cl | H | O | CH₂ | 2 |
| 5c | H | Cl | H | O | CH₂ | 3 |
| 5d | H | Cl | CH₃ | O | CH₂ | 1 |
| 5e | H | Cl | CH₃ | O | CH₂ | 2 |
| 5f | H | Cl | CH₃ | O | CH₂ | 3 |
| 5g | H | Cl | Cl | O | CH₂ | 1 |
| 5h | H | Cl | Cl | O | CH₂ | 2 |
| 5i | H | Cl | Cl | O | CH₂ | 4 |
| 5j | Cl | Cl | H | NH | C=O | 0 |
| 5k | Cl | Cl | H | NH | C=O | 1 |
| 5l | Cl | Cl | H | NH | C=O | 2 |

PYRROLO[2,1-C][1,4]BENZODIAZEPINE HYBRIDS AND A PROCESS FOR THE PREPARATION THEREOF

CROSS REFERENCE TO RELATED APPLICATION

This application is a utility application and claims the benefit under 35 USC § 119(a) of India Application No. 1823/DEL/2006 filed Aug. 14, 2006. This disclosure of the prior application is considered part of and is incorporated by reference in the disclosure of this application.

BACKGROUND OF THE INVENTION

1. Field of the Invention

The present invention relates to Benzophenone linked pyrrolo[2,1-c][1,4]benzodiazepine hybrids and a process for the preparation thereof. More particularly it relates to 7-methoxy-8-{n-[2-benzoyl-(4-chlorophenyloxy)alkyl]oxy}-(11aS)-1,2,3,11a-tetrahydro-5H-pyrrolo[2,1-c][1,4]benzodiazepine-5-one with aliphatic chain length variations useful as anticancer (antitumour) agent. The structural formula of these Benzophenone linked pyrrolo[2,1-c][1,4]benzodiazepines hybrids is given below.

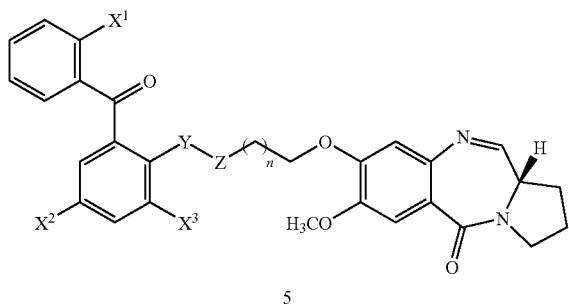

Formula 5

$X^1, X^2, X^3$ = H or Cl or $CH_3$
Y = O or NH
Z = C=O or $CH_2$

2. Background Information

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665.; Kohn, K. W. and Speous, C. L. *J. Mol. Biol.*, 1970, 51, 551.; Hurley, L. H.; Gairpla, C. and Zmijewski, M. *Biochem. Biophys. Acta.*, 1977, 475, 521.; Kaplan, D. J. and Hurley, L. H. *Biochemistry*, 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S. and Hurley, L. H. *J. Org. Chem.* 1996, 61, 8141).

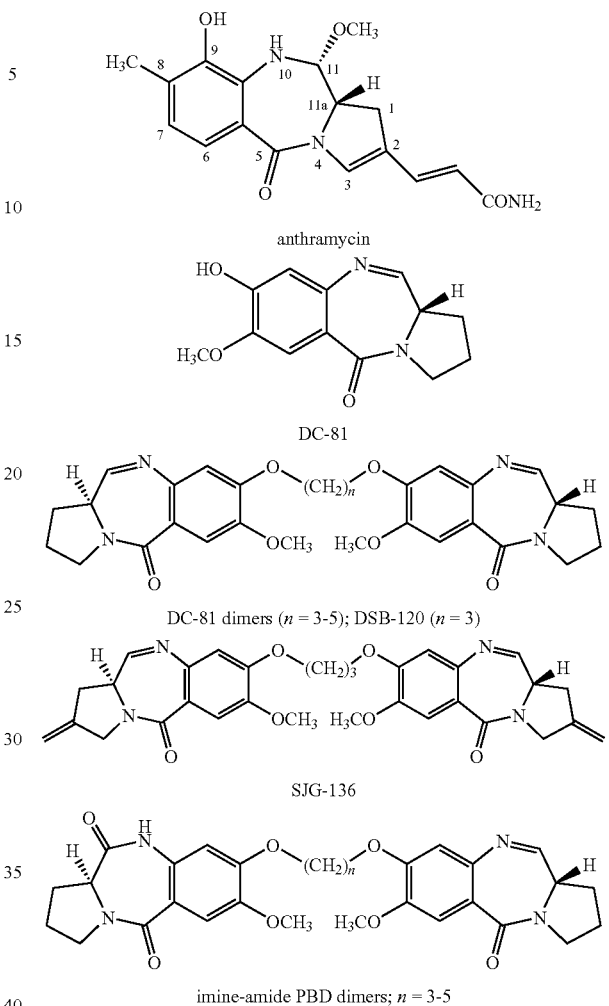

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679). Recently, some new pyrrolobenzodiazepine (PBD) hybrids have been synthesized that have significant DNA binding ability and potent antitumour activity. (Kamal, A.; Srinivas, O.; Ramulu, P.; Ramesh, G.; Kumar, P. P. *Bioorg. Med. Chem. Lett.* 2003, 13, 3577).

Naturally occurring pyrrolo[2,1-c][1,4]benzodiazepines belong to a group of antitumour antibiotics derived from *Streptomyces* species. Recently, there is much impetus for the PBD systems as they can recognize and bind to specific sequence of DNA. Examples of naturally occurring PBDs include anthramycin, DC-81, tomaymycin, sibiromycin and neothramycin.

However, the clinical efficacy for these antibiotics is hindered by several limitations, such as poor water solubility, cardio toxicity, development of drug resistance and metabolic inactivation.

OBJECTIVES OF THE INVENTION

The main objective of the present invention is to provide Novel Benzophenone pyrrolo[2,1-c][1,4]benzodiazepine hybrids, useful as antitumour agents.

Yet another object of this invention is to provide a process for the preparation of Novel Benzophenone pyrrolo[2,1-c][1,4]benzodiazepine hybrids.

SUMMARY OF THE INVENTION

Accordingly the present invention provides a novel benzophenone linked pyrrolo[2,1-c][1,4]benzodiazepine hybrid of general formula 5

Formula 5

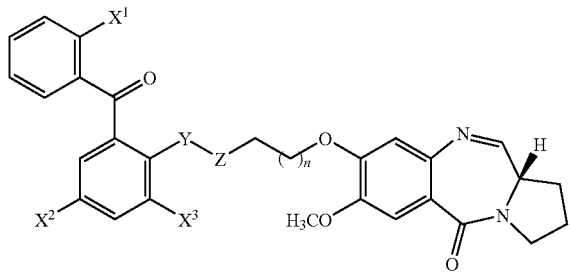

5

$X^1, X^2, X^3$ = H or Cl or $CH_3$
Y = O or NH
Z = C═O or $CH_2$

Where in, n=1-4.

In an embodiment of the present invention the novel benzophenone linked pyrrolo[2,1-c][1,4]benzodiazepine hybrid is represented by the group of the following compounds:

7-methoxy-8-{3-[2-benzoyl-(4-chlorophenyloxy)propoxy]}-(11aS)-1,2,3,11a-tetrahydro-5H-pyrrolo[2,1-c][1,4]benzodiazepine-5-one (5a);

7-methoxy-8-{4-[2-benzoyl-(4-chlorophenyloxy)butoxy]}-(11aS)-1,2,3,11a-tetrahydro-5H-pyrrolo[2,1-c][1,4]benzodiazepine-5-one (5b);

7-methoxy-8-{5-[2-benzoyl-(4-chlorophenyloxy)pentoxy]}-(11aS)-1,2,3,11a-tetrahydro-5H-pyrrolo[2,1-c][1,4]benzodiazepine-5-one (5c);

7-methoxy-8-{3-[2-benzoyl-(4-chloro-6-methylphenyloxy)propoxy]}-(11aS)-1,2,3,11a-tetrahydro-5H-pyrrolo[2,1-c][1,4]benzodiazepine-5-one (5d);

7-methoxy-8-{3-[2-benzoyl-(4-chloro-6-methylphenyloxy)butoxy]}-(11aS)-1,2,3,11a-tetrahydro-5H-pyrrolo[2,1-c][1,4]benzodiazepine-5-one (5e);

7-methoxy-8-{3-[2-benzoyl-(4-chloro-6-methylphenyloxy)pentoxy]}-(11aS)-1,2,3,11a-tetrahydro-5H-pyrrolo[2,1-c][1,4]benzodiazepine-5-one (5f);

7-methoxy-8-{3-[2-benzoyl-(4,6-dichlorophenyloxy)propoxy]}-(11aS)-1,2,3,11a-tetra hydro-5H-pyrrolo[2,1-c][1,4]benzodiazepine-5-one (5g);

7-methoxy-8-{3-[2-benzoyl-(4,6-dichlorophenyloxy)butoxy]}-(11aS)-1,2,3,11a-tetra hydro-5H-pyrrolo[2,1-c][1,4]benzodiazepine-5-one (5h);

7-methoxy-8-{3-[2-benzoyl-(4,6-di-chlorophenyloxy)hexyloxy]}-(11aS)-1,2,3,11a-tetrahydro-5H-pyrrolo[2,1-c][1,4]benzodiazepine-5-one (5i);

7-Methoxy-8-{N1-[4-chloro-2-(2-chlorobenzoyl)phenyl]2-oxyacetamido}-(11aS)-1,2,3,11a-tetrahydro-5H-pyrrolo[2,1-c][1,4]benzodiazepine-5-one (5j);

7-Methoxy-8-{N1-[4-chloro-2-(2-chlorobenzoyl)phenyl]2-oxypropinamido}-(11aS)-1,2,3,11a-tetrahydro-5H-pyrrolo[2,1-c][1,4]benzodiazepine-5-one (5k);

7-Methoxy-8-{N1-[4-chloro-2-(2-chlorobenzoyl)phenyl]2-oxybutanamido}-(11aS)-1,2,3,11a-tetrahydro-5H-pyrrolo[2,1-c][1,4]benzodiazepine-5-one (5l).

In yet another embodiment the structural formula of the representative compounds of benzophenone linked pyrrolo[2,1-c][1,4]benzodiazepine hybrid are:

Formula 5a-c

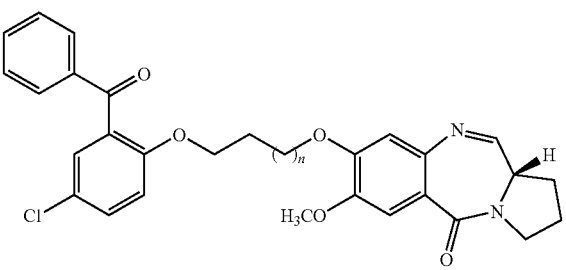

n = 1, 2 3

Formula 5d-f

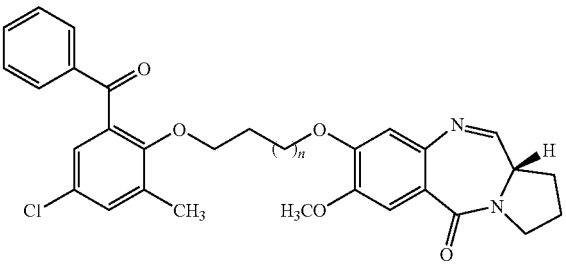

n = 1, 2 or 3

Formula 5g-i

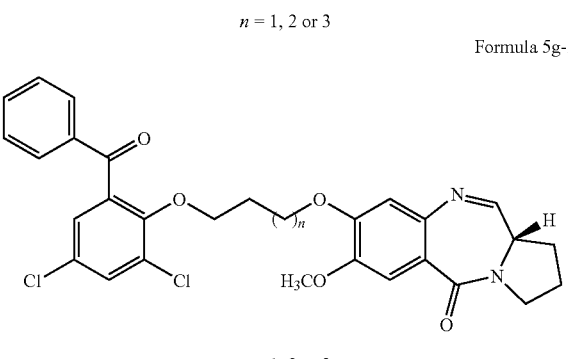

n = 1, 2 or 3

Formula 5j-l

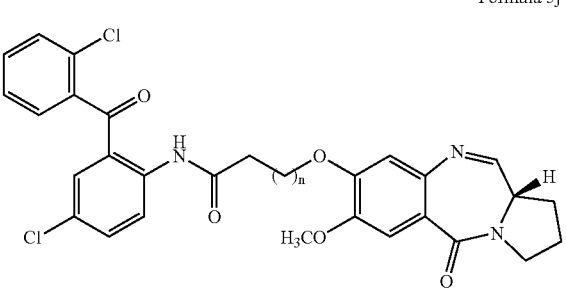

n = 1, 2 or 3

In yet another embodiment the novel benzophenone linked pyrrolo[2,1-c][1,4]benzodiazepine hybrid exhibits an in vitro anticancer/antitumour activity against human cancer cell lines selected from the group consisting of lung (Hop-62), cervix (SiHa), breast (MCF7, Zr-75-1), colon (Colo205), prostate (DU145, PC3) and oral (DWD, HT1080) cell lines.

In yet another embodiment the concentration of benzophenone linked pyrrolo[2,1-c][1,4]benzodiazepine hybrid used for in vitro activity against Colo205 for IC50 is in the range of 17 to 80 μm, at an exposure period of at least 48 hrs.

In yet another embodiment the concentration of benzophenone linked pyrrolo[2,1-c][1,4]benzodiazepine hybrids used for in vitro activity against DU145 for IC50 is in the range of 16 to 80 μm, at an exposure period of at least 48 hrs.

In yet another embodiment the concentration of benzophenone linked pyrrolo[2,1-c][1,4]benzodiazepine hybrids used for in vitro activity against DWD for IC50 is in the range of 6 to 80 μm, at an exposure period of at least 48 hrs.

In yet another embodiment the concentration of benzophenone linked pyrrolo[2,1-c][1,4]benzodiazepine hybrids used for in vitro activity against HoP62 for IC50 is in the range of 13 to 40 μm, at an exposure period of at least 48 hrs.

In yet another embodiment the concentration of benzophenone linked pyrrolo[2,1-c][1,4]benzodiazepine hybrids used for in vitro activity against HT1080 for IC50 is in the range of 6 to 30 μm, at an exposure period of at least 48 hrs.

In yet another embodiment the concentration of benzophenone linked pyrrolo[2,1-c][1,4]benzodiazepine hybrids used for in vitro activity against MCF7 for IC50 is in the range of 27 to about 80 μm, at an exposure period of at least 48-hrs.

In yet another embodiment the concentration of benzophenone linked pyrrolo[2,1-c][1,4]benzodiazepine hybrids used for in vitro activity against PC3 for IC50 is in the range of 9 to about 80 μm, at an exposure period of at least 48 hrs.

In yet another embodiment the concentration of benzophenone linked pyrrolo[2,1-c][1,4]benzodiazepine hybrids used for in vitro activity against SiHa for IC50 is in the range of 25 to about 80 μm, at an exposure period of at least 48 hrs.

In yet another embodiment the concentration of benzophenone linked pyrrolo[2,1-c][1,4]benzodiazepine hybrids used for in vitro activity against Zr-75-1 for IC50 is in the range of 24 to about 80 μm, at an exposure period of at least 48 hrs.

The present invention further provides a pharmaceutical composition comprising benzophenone linked pyrrolo[2,1-c][1,4]benzodiazepine hybrid, its derivatives, analogues, salts or mixture thereof optionally with pharmaceutically acceptable carriers, adjuvants and additives.

In yet another embodiment the benzophenone linked pyrrolo[2,1-c][1,4]benzodiazepine hybrid used is represented by a general formula 5, Formula 5

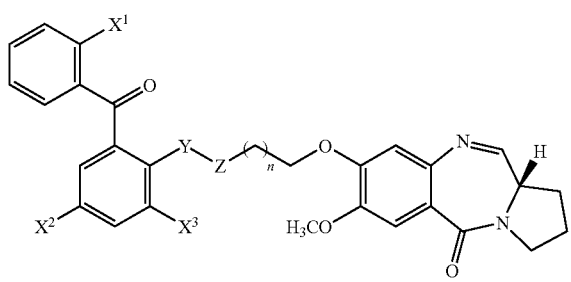

$X^1, X^2, X^3$ = H or Cl or CH$_3$
Y = O or NH
Z = C=O or CH$_2$ wherein n=1, 2, 3 or 4.

The present invention further provides a process for the preparation of benzophenone linked pyrrolo[2,1-c][1,4]benzodiazepine hybrid of formula 5, Formula 5

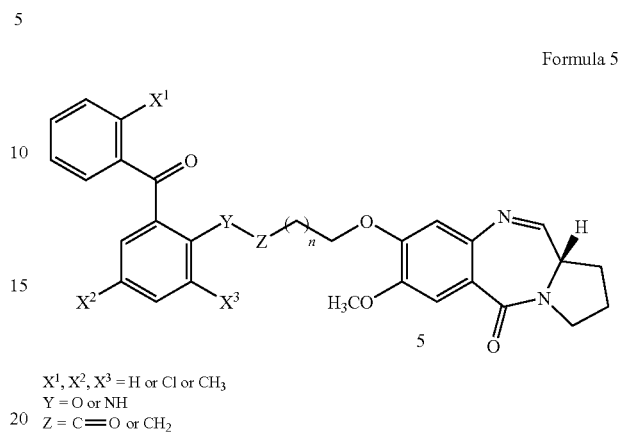

$X^1, X^2, X^3$ = H or Cl or CH$_3$
Y = O or NH
Z = C=O or CH$_2$ wherein n=1, 2, 3 or 4, the said process comprising the steps of:

a) reacting (2S)-N-(4-hydroxy-3-methoxy-2-nitrobenzoyl)pyrrolidine-2-carboxaldehyde diethylthioacetal of formula 2

2

[2-(n-bromoalkyl)-n-chlorophenyl)(phenyl)methanone or acetamide of formula 1, wherein $X^1$, $X^2$ and $X^3$ are selected from the group consisting of H, Cl and CH$_3$; Y is selected from O and NH; Z is selected from C=O and CH$_2$; n=1 to 4, in an aprotic water miscible organic solvent, in the presence of anhydrous mild inorganic base, under refluxing temperature in an oil bath, for a period of about 48 hrs, followed by the removal of inorganic base by filtration and evaporating the organic solvent to obtain the resultant crude product and purifying it by known method to obtain the desired product of (2S)-N-{n benzoyl(phenyloxy)alkoxy/[(n benzoyl)phenyl]2-oxyacetamido]5-methoxy-2-nitrobenzoyl}-pyrrolidine-2-carboxaldehyde diethylthioacetal of formula 3,

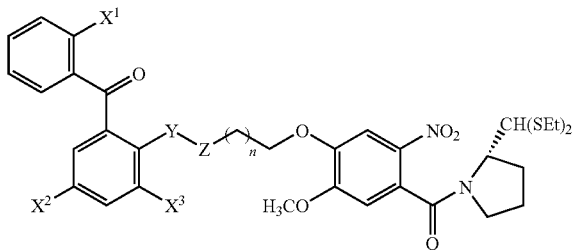

wherein $X^1$, $X^2$ and $X^3$ are selected from the group consisting of H, Cl and $CH_3$; Y is selected from O and NH; Z is selected from C=O and $CH_2$; n=1 to 4, b) reducing (2S)-N-{n benzoyl(phenyloxy)alkoxy/(n benzoyl)phenyl]2 oxyacetamido]-5-methoxy-2-nitrobenzoyl}-pyrrolidine-2-carboxaldehyde diethylthioacetal of formula 3 with anhydrous tin chloride, in an alcohol, under reflux, followed by the evaporation of alcohol and adjusting the pH of the resultant product layer to about 8 by using a base, followed by extraction with ethyl acetate and washing the combined organic phase with brine solution and evaporating the solvent to obtain the desired (2S)-N-{n-benzoyl(phenyloxy)alkoxy/[(n-benzoyl)phenyl]2-oxyacetamido]-5-methoxy-2-aminobenzoyl}-pyrrolidine-2-carboxaldehyde diethylthioacetal of formula 4,

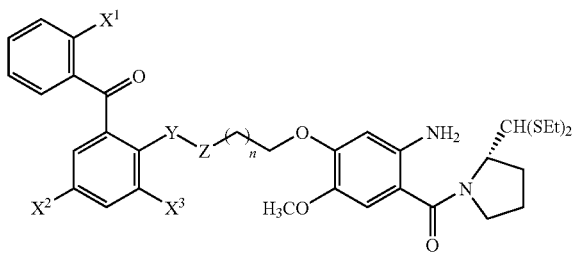

wherein $X^1$, $X^2$ and $X^3$ are selected from the group consisting of H, Cl and $CH_3$; Y is selected from O and NH; Z is selected from C=O and $CH_2$; n=1 to 4, c) reacting (2S)-N-{n benzoyl(phenyloxy)alkoxy/[(n benzoyl)phenyl]2-oxyacetamido]-5-methoxy-2-aminobenzoyl}-pyrrolidine-2-carboxaldehyde diethylthioacetal of formula 4 with mercurous chloride, in a mixture of water and organic solvent, in the presence of mild inorganic base, under stirring, at a temperature of about 20-30° C., for a period of 8-12 hrs, followed by the extraction of yellow organic supernatant and washing with sodium bi carbonate and brine, respectively, and evaporating the organic layer, under reduced pressure to obtain the desired product of benzophenone linked pyrrolo[2,1-c][1,4]benzodiazepine hybrid of formula 5.

In yet another embodiment the mild inorganic base used in steps (a) & (c) is calcium carbonate.

In yet another embodiment the aprotic organic solvent used in step (a) is acetone and acetonitrile In yet another embodiment the organic solvent used in step (c) is acetonitrile and acetone In yet another embodiment the alcohol used in step (b) is selected from methanol and ethanol.

In yet another embodiment the compounds of formula 5 obtained are represented by a group of the following compounds:

7-methoxy-8-{3-[2-benzoyl-(4-chlorophenyloxy)propoxy]}-(11aS)-1,2,3,11a-tetra hydro-5H-pyrrolo[2,1-c][1,4]benzodiazepine-5-one (5a);

7-methoxy-8-{4-[2-benzoyl-(4-chlorophenyloxy)butoxy]}-(11aS)-1,2,3,11a-tetrahydro-5H-pyrrolo[2,1-c][1,4]benzodiazepine-5-one (5b);

7-methoxy-8-{5-[2-benzoyl-(4-chlorophenyloxy)pentoxy]}-(11aS)-1,2,3,11a-tetrahydro-5H-pyrrolo[2,1-c][1,4]benzodiazepine-5-one (5c);

7-methoxy-8-{3-[2-benzoyl-(4-chloro-6-methylphenyloxy)propoxy]}-(11aS)-1,2,3,11a-tetrahydro-5H-pyrrolo[2,1-c][1,4]benzodiazepine-5-one (5d);

7-methoxy-8-{3-[2-benzoyl-(4-chloro-6-methylphenyloxy)butoxy]}-(11aS)-1,2,3,11a-tetrahydro-5H-pyrrolo[2,1-c][1,4]benzodiazepine-5-one (5e);

7-methoxy-8-{3-[2-benzoyl-(4-chloro-6-methylphenyloxy)pentoxy]}-(11aS)-1,2,3,11a-tetrahydro-5H-pyrrolo[2,1-c][1,4]benzodiazepine-5-one (5f);

7-methoxy-8-{3-[2-benzoyl-(4,6-dichlorophenyloxy)propoxy]}-(11aS)-1,2,3,11a-tetrahydro-5H-pyrrolo[2,1-c][1,4]benzodiazepine-5-one (5g);

7-methoxy-8-{3-[2-benzoyl-(4,6-dichlorophenyloxy)butoxy]}-(11aS)-1,2,3,11a-tetra hydro-5H-pyrrolo[2,1-c][1,4]benzodiazepine-5-one (5h);

7-methoxy-8-{3-[2-benzoyl-(4,6-di-chlorophenyloxy)hexyloxy]}-(11aS)-1,2,3,11a-tetrahydro-5H-pyrrolo[2,1-c][1,4]benzodiazepine-5-one (5i);

7-Methoxy-8-{N1-[4-chloro-2-(2-chlorobenzoyl)phenyl]2-oxyacetamido}-(11aS)-1,2,3,11a-tetrahydro-5H-pyrrolo[2,1-c][1,4]benzodiazepine-5-one (5j);

7-Methoxy-8-{N1-[4-chloro-2-(2-chlorobenzoyl)phenyl]2-oxypropinamido}-(11aS)-1,2,3,11a-tetrahydro-5H-pyrrolo[2,1-c][1,4]benzodiazepine-5-one (5k);

7-Methoxy-8-{N1-[4-chloro-2-(2-chlorobenzoyl)phenyl]2-oxybutanamido}-(11aS)-1,2,3,11a-tetrahydro-5H-pyrrolo[2,1-c][1,4]benzodiazepine-5-one (5l).

In still another embodiment the benzophenone linked pyrrolo[2,1-c][1,4]benzodiazepine hybrid of formula 5a-m exhibits an in vitro anticancer/antitumour activity against human cancer cell lines selected from the group consisting of lung, cervix, breast, colon, prostate and oral cell lines.

BRIEF DESCRIPTION OF THE DRAWING

The attached drawing shows chemical structures and substituents for compounds 5a through 5l.

DETAILED DESCRIPTION OF THE INVENTION

Accordingly, the present invention provides a process for preparation of pyrrolo[2,1-c][1,4]benzodiazepine hybrids of formula 5 of the drawing accompanying the specification where n=1-5, which comprises reacting {2-[(n-bromoalkyl)-3,5 dichloro phenyl](phenyl)methanone of formula 1 with 2S-N-(4-hydroxy-5-methoxy-2-nitrobenzoyl)pyrrolidine-2-carboxaldehyde diethylthioacetal of formula 2 in presence of $CH_3COCH_3/K_2CO_3$ for a period of 48 hr. with isolating (2S)-N-{3-[benzoyl(4-chlorophenyloxy)propyl]oxy-5-methoxy-2-nitrobenzoyl}pyrrolidine-2-carboxaldehyde diethylthioacetal of formula 3 by conventional methods, reducing the above nitro compound of formula 3 with $SnCl_2.2H_2O$ in presence of organic solvent with reflux temperature, resulting with the formation of (2S)-N-{3-[benzoyl(4-chlorophenyloxy]propoxy]}-5-methoxy-2-aminobenzoyl}pyrrolidine-2-carboxaldehyde diethylthioacetal 4 respectively by known methods, reacting the above said amino compound of formula 4 with known deprotecting agents in a conventional manner to give novel pyrrolo[2,1-c][1,4]benzodiazepine hybrids of formula 5, where 'n' is as stated above.

The precursors, [2-(n-bromoalkyl)-n-chlorophenyl)(phenyl)methanone of formula 1 (Liou, J. P.; Chang, C. W.; Song, J. S.; Yang, Y. N.; Yeh, C. F.; Tseng, H. Y.; Lo, Y. K.; Chang, Y. L.; Chang, C. M.; Hsieh, H. P.; J. Med. Chem. 2002, 45, 2556-2562) and (2S)-N-(4-hydroxy-5-methoxy-2-nitrobenzoyl)pyrrolidine-2-carboxaldehyde diethyl-thioacetal of formula 2 (Thurston, D. E.; Morris, S. J.; Hartley, J. A. *Chem. Commun.* 1996, 563-565) have been prepared by literature methods.

Some representative compounds of formula 5 for the present inventions are given below:
a) 7-Methoxy-8-{3-[2-benzoyl-(4-chlorophenyloxy)propoxy]}-(11aS)-1,2,3,11a-tetrahydro-5H-pyrrolo[2,1-c][1,4]benzodiazepine-5-one.
b) 7-Methoxy-8-{4-[2-benzoyl-(4-chlorophenyloxy)butoxy]}-(11aS)-1,2,3,11a-tetrahydro-5H-pyrrolo[2,1-c][1,4]benzodiazepine-5-one.
c) 7-Methoxy-8-{3-[2-benzoyl-(4,6-dichlorophenyloxy)propoxy]}-(11aS)-1,2,3,11a-tetrahydro-5H-pyrrolo[2,1-c][1,4]benzodiazepine-5-one;
d) 7-Methoxy-8-{3-[2-benzoyl-(4,6-dichlorophenyloxy)hexyloxy]}-(11aS)-1,2,3,11a-tetrahydro-5H-pyrrolo[2,1-c][1,4]benzodiazepine-5-one;
e) 7-Methoxy-8-{N1-[4-chloro-2-(2-chlorobenzoyl)phenyl]2-oxyacetamido}-(11aS)-1,2,3,11a-tetrahydro-5H-pyrrolo[2,1-c][1,4]benzodiazepine-5-one.

These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. This resulted in design and synthesis of new congeners as illustrated in Scheme-1, which comprise:
1. The ether linkage at C-8 position of DC-81 intermediates with [2-(n-bromoalkyl)-5-chlorophenyl(phenyl)methanone moiety.
2. Refluxing the reaction mixtures for 48 h.
3. Synthesis of C-8 linked PBD antitumour antibiotic hybrid imines.
4. Purification by column chromatography using different solvents like ethyl acetate, hexane, dichloromethane and methanol.

The following examples are given by way of illustration and therefore should not be construed to the present limit of the scope of invention.

EXAMPLE 1

To a solution of (2S)-N-(4-hydroxy-3-methoxy-2-nitrobenzoyl)pyrrolidine-2-carboxaldehyde diethylthioacetal 2 (500 mg, 1.25 mmol) in dry acetone (20 mL) was added anhydrous potassium carbonate (862 mg, 6.25 mmol) and [2-(3-bromopropyl)-5-chlorophenyl](phenyl)methanone 1 (441 mg, 1.25 mmol). The reaction mixture was refluxed for 48 h and the reaction was monitored by TLC using ethyl acetate-hexane (4:6) as a solvent system. The potassium carbonate was then removed by suction filtration and the solvent was evaporated under vacuum to afford the crude product. This was further purified by column chromatography using ethyl acetate:hexane (3:7) as a solvent system to obtain the pure product 3 (672 mg, 80% yield).

$^1$H NMR (CDCl$_3$) δ1.16-1.34 m, 6H), 1.58-2.14 (m, 6H), 2.28-2.41 (m, 3H), 2.60-2.93 (m, 4H), 3.14-3.28 (m, 2H), 3.98 (s, 3H), 4.17-4.21 (t, 2H), 4.54-4.66 (m, 1H), 6.78 (s, 1H), 6.85-6.95 (d, J=4.87 1H), 7.30-7.60 (m, 7H), 7.65-7.80 (d, 1H); FABMS: 672 (M+H);

(2S)-N-{3-[Benzoyl(4-chlorophenyloxy)propoxy]}-5-methoxy-2-nitrobenzoyl}-pyrrolidine-2-carboxaldehyde diethylthioacetal of formula 3 (500 mg, 0.74 mmol) was dissolved in methanol (10 mL), SnCl$_2$.2H$_2$O (839 mg, 3.7 mmol) was added and refluxed until the TLC indicated the completion of the reaction. The methanol was evaporated by vacuum and the aqueous layer was then adjusted to pH 8 with 10% NaHCO$_3$ solution and extracted with ethyl acetate (2×30 mL). The combined organic phase was dried over Na$_2$SO$_4$ and evaporated under vacuum to afford the crude amino diethylthioacetal 4 (450 mg, 95% yield), which was directly used in the next step.

A solution of (2S)-N-{3-[benzoyl(4-chlorophenyloxy)propoxy]}-5-methoxy-2-amino-benzoyl}pyrrolidine-2-carboxaldehyde diethylthioacetal 4 (400 mg, 0.62 mmol), HgCl$_2$ (372 mg, 1.37 mmol) and CaCO$_3$ (157 mg, 1.55 mmol) in acetonitrile-water (4:1) was stirred slowly at room temperature for overnight until complete loss of starting material as indicated by the TLC. The clear organic supernatant liquid was extracted with ethyl acetate and washed with saturated 5% NaHCO$_3$ (20 mL), brine (20 mL) and the combined organic phase was dried over Na$_2$SO$_4$. The organic layer was evaporated in vacuum to afford a white solid, which was first eluted on a column chromatography with ethyl acetate to remove mercuric salts, and then with ethyl acetate to obtain the pure product 5a (195 mg, 60% yield).

$^1$H NMR (CDCl$_3$) δ1.90-2.12 (m, 2H), 2.22-2.46 (m, 3H), 3.50-3.88 (m, 3H), 3.95 (s, 3H), 4.24-4.35 (m, 4H), 6.54 (s, 1H), 6.88-6.96 (m, 1H), 7.24-7.26 (s, 1H), 7.30-7.45 (m, 3H), 7.46-7.52 (m, 2H), 7.66-7.78 (m, 2H); FABMS: 524 (M+H)

EXAMPLE 2

To a solution of (2S)-N-(4-hydroxy-3-methoxy-2-nitrobenzoyl)pyrrolidine-2-carboxaldehyde diethylthioacetal 2 (512 mg, 1.28 mmol) in dry acetone (20 mL) was added anhydrous potassium carbonate (883 mg, 6.40 mmol) and [2-(4-bromobutoxy)-5-chlorophenyl](phenyl)methanone 1 (469 mg, 1.28 mmol). The reaction mixture was refluxed for 48 h and the reaction was monitored by TLC using ethyl acetate-hexane (2:8) as a solvent system. The potassium carbonate was then removed by suction filtration and the solvent was evaporated under vacuum to afford the crude product. This was further purified by column chromatography using ethyl acetate:hexane (3:7) as a solvent system to obtain the pure product 3 (721 mg, 82% yield).

$^1$H NMR (CDCl$_3$) δ1.18-1.38 (m, 8H), 1.59-2.18 (m, 6H), 2.26-2.42 (m, 3H), 2.53-2.90 (m, 4H), 3.18-3.29 (m, 2H), 3.96 (s, 3H), 4.18 (t, 2H), 4.54-4.55 (m, 1H), 6.73 (s, 1H), 7.4 (s, 1H), 7.6-7.68 (m, 3H), 7.75-7.85 (m, 3H), 7.98-8.0 (m, 2H); FABMS: 687 (M+H)

2S)-N-{3-[Benzoyl(4-chlorophenyloxy)butoxy]}-5-methoxy-2-nitrobenzoyl}pyrrolidine-2-carboxaldehyde diethylthioacetal of formula 3 (600 mg, 0.87 mmol) was dissolved in methanol (10 mL), SnCl$_2$.2H$_2$O (982 mg, 4.3 mmol) was added and refluxed until the completion of the reaction which was monitored by TLC. The methanol was evaporated by vacuum and the aqueous layer was then adjusted to pH 8 with 10% NaHCO$_3$ solution and extracted with ethyl acetate (2×30 mL). The combined organic phase was dried over Na$_2$SO$_4$ and evaporated under vacuum to afford the crude amino diethylthioacetal 4 (545 mg, 95% yield), which was directly used in the next step.

A solution of 2S)-N-{3-[benzoyl(4-chlorophenyloxy)butoxy]}-5-methoxy-2-aminoben-zoyl}pyrrolidine-2-carboxaldehyde diethylthioacetal 4 (500 mg, 0.76 mmol), HgCl$_2$ (613 mg, 1.82 mmol) and CaCO$_3$ (191 mg, 1.90 mmol) in acetonitrile-water (4:1) was stirred slowly at room temperature for overnight until complete consumption of starting material as indicated by the TLC. The clear organic supernatant liquid was extracted with saturated 5% NaHCO$_3$ (20 mL), brine (20 mL) and the combined organic phase was dried over Na$_2$SO$_4$. The organic layer was evaporated in vacuum to afford a white solid, which was first eluted on a column chromatography with ethyl acetate to remove mercuric salts, and then with ethyl acetate to obtain the pure product 5b (225 mg, 55% yield).

$^1$H NMR (CDCl$_3$) δ1.80-2.25 (m, 8H), 2.26-2.4 (m, 4H), 3.6 (s, 3H), 3.80-3.98 (m, 1H), 4.0-4.3 (m, 4H), 6.54 (s, 1H), 6.88-6.96 (m, 1H), 7.24-7.26 (s, 1H), 7.30-7.45 (m, 3H), 7.46-7.52 (m, 2H), 7.66-7.78 (m, 2H); FABMS: 538 (M+H)

EXAMPLE 3

To a solution of (2S)-N-(4-hydroxy)-3-methoxy-2-nitrobenzoyl)pyrrolidine-2-carboxaldehyde diethylthioacetal 2 (400 mg, 1 mmol) in dry acetone (20 mL) was added anhydrous potassium carbonate (686 mg, 5 mmol) and [2-(-bromobutoxy)-3,5-dichloro phenyl](phenyl)methanone 1 (402 mg, 1 mmol). The reaction mixture was refluxed in an oil bath for 48 h and the reaction was monitored by TLC using ethyl acetate-hexane (4:6) as a solvent system. The potassium carbonate was then removed by suction filtration and the solvent was evaporated under vacuum to afford the crude product. This was further purified by column chromatography using ethyl acetate:hexane (3:7) as a solvent system to obtain the pure product 3 (578 mg, 82% yield).

$^1$H NMR (CDCl$_3$) δ1.18-1.38 (m, 8H), 1.59-2.18 (m, 6H), 2.26-2.42 (m, 3H), 2.53-2.90 (m, 4H), 3.18-3.29 (m, 2H), 3.96 (s, 3H), 4.18 (t, 2H), 4.54-4.55 (m, 1H), 6.73 (s, 1H), 7.4 (s, 1H), 7.6-7.68 (m, 3H), 7.75-7.85 (m, 3H), 7.98-8.0 (m, 2H); FABMS: 706 (M+H)

2S)-N-{3-[2-Benzoyl(4,6-dichlorophenyloxy)butoxy]}-5-methoxy-2-nitrobenzoyl}pyrrolidine-2-carboxaldehyde diethylthioacetal of formula 3 (500 mg, 0.70 mmol) was dissolved in methanol (10 mL), SnCl$_2$.2H$_2$O (796 mg, 3.54 mmol) was added and refluxed until the TLC indicated the completion of the reaction. The methanol was then evaporated in vacuum and the aqueous layer was then adjusted to pH 8 with 10% NaHCO$_3$ solution and extracted with ethyl acetate (60 mL). The combined organic phase was dried over Na$_2$SO$_4$ and evaporated under vacuum to afford the crude amino diethyl thioacetal 4 (470 mg, 96% yield), which was directly used in the next step.

A solution of 2S)-N-{3-[2-benzoyl(4,6-dichloro phenyloxy)butoxy]}-5-methoxy-2-aminobenzoyl}pyrrolidine-2-carboxaldehyde diethylthioacetal of formula 4 (400 mg, 0.57 mmol), HgCl$_2$ (377 mg, 1.3 mmol) and CaCO$_3$ (146 mg, 1.44 mmol) in acetonitrile-water (4:1) was stirred slowly at room temperature overnight until complete consumption of starting material as indicated by the TLC. The clear organic supernatant liquid was extracted with ethyl acetate and washed with saturated 5% NaHCO$_3$ (20 mL), brine (20 mL) and the combined organic phase was dried over Na$_2$SO$_4$. The organic layer was evaporated in vacuum to afford a white solid, which was first eluted on a column chromatography with ethyl acetate to remove mercuric salts, and then with ethyl acetate to obtain the pure product 5c (183 mg, 56% yield).

$^1$H NMR (CDCl$_3$) δ1.80-2.25 (m, 8H), 2.26-2.4 (m, 4H), 3.6 (s, 3H), 3.80-3.98 (m, 1H), 4.0-4.3 (m, 4H), 6.54 (s, 1H), 7.24 (s, 1H), 7.3-7.45 (m, 3H), 7.45-7.52 (m, 2H), 7.65-7.75 (m, 2H); FABMS: 567 (M+H)

EXAMPLE 4

To a solution of (2S)-N-(4-hydroxy)-3-methoxy-2-nitrobenzoyl)pyrrolidine-2-carboxaldehyde diethylthioacetal of formula 2 (400 mg, 1 mmol) in dry acetone (20 mL) was added anhydrous potassium carbonate (690 mg, 5 mmol) and {2-(6-bromohexyl) oxy]-3,5-dichloro phenyl}(phenyl)methanone 1 (430 mg, 1 mmol). The reaction mixture was refluxed in an oil bath for 48 h and the reaction was monitored by TLC using ethyl acetate-hexane (4:6) as a solvent system. The potassium carbonate was then removed by suction filtration and the solvent was evaporated under vacuum to afford the crude product. This was further purified by column chromatography using ethyl acetate:hexane (3:7) as a solvent system to obtain the pure product 3 (614 mg, 82% yield).

$^1$H NMR (CDCl$_3$) δ1.2-1.38 (m, 8H), 1.6-2.20 (m, 10H), 2.3-2.42 (m, 3H), 2.53-2.90 (m, 4H), 3.2-3.29 (m, 2H), 3.94 (s, 3H), 4.10 (t, 2H), 4.52-4.54 (m, 1H), 6.43 (s, 1H), 7.15-7.25 (s, 1H), 7.4-7.65 (m, 6H), 7.72-7.85 (d, 1H); FABMS: 749 (M+H)

(2S)-N-{3-[2-benzoyl(4,6-dichlorophenyloxy) hexyloxy]}-5-methoxy-2-nitrobenzoyl}pyrrolidine-2-carboxaldehyde diethylthioacetal of formula 3 (500 mg, 0.66 mmol) was dissolved in methanol (10 mL), SnCl$_2$.2H$_2$O (754 mg, 3.33 mmol) was added and refluxed until the TLC indicated the completion of the reaction. The methanol was then evaporated in vacuum and the aqueous layer was then adjusted to pH 8 with 10% NaHCO$_3$ solution and extracted with ethyl acetate (60 mL). The combined organic phase was dried over Na$_2$SO$_4$ and evaporated under vacuum to afford the crude amino diethyl thioacetal 4 (460 mg, 96% yield), which was directly used in the next step.

A solution of (2S)-N-{3-[2-benzoyl(4,6-dichlorophenyloxy)hexyloxy]}-5-methoxy-2-aminobenzoyl}pyrrolidine-2-carboxaldehyde diethylthioacetal 4 (400 mg, 0.55 mmol), HgCl$_2$ (377 mg, 1.32 mmol) and CaCO$_3$ (140 mg, 1.39 mmol) in acetonitrile-water (4:1) was stirred slowly at room temperature for overnight until complete consumption of starting material as indicated by the TLC. The clear organic supernatant liquid was extracted with ethyl acetate and washed with saturated 5% NaHCO$_3$ (20 mL), brine (20 mL) and the combined organic phase was dried over Na$_2$SO$_4$. The organic layer was evaporated in vacuum and to afford a white solid, which was first eluted on a column chromatography with ethyl acetate to remove mercuric salts, and then with ethyl acetate to obtain the pure product 5c (185 mg, 56% yield).

$^1$H NMR (CDCl$_3$) δ1.60-2.19 (m, 8H), 2.15-2.25 (m, 8H), 3.55-3.90 (m, 4H), 3.95 (s, 1H), 4.15-4.35 (m, 4H), 6.74 (s, 1H), 7.24 (s, 1H), 7.3-7.45 (m, 3H), 7.45-7.52 (m, 2H), 7.65-7.75 (m, 2H); FABMS: 595 (M+H)

EXAMPLE 5

To a solution of (2S)-N-(4-hydroxy)-3-methoxy-2-nitrobenzoyl)pyrrolidine-2-carboxaldehyde diethylthioacetal 2 (400 mg, 1 mmol) in dry acetone (20 mL) was added anhydrous potassium carbonate (690 mg, 5 mmol) and N1-[4-chloro-2-(2-chlorobenzoyl)phenyl]-2-chloro acetamide 1 (342 mg, 1 mmol). The reaction mixture was refluxed in an oil bath for 48 h and the reaction was monitored by TLC using ethyl acetate-hexane (4:6) as a solvent system. The potassium carbonate was then removed by suction filtration and the solvent was evaporated under vacuum to afford the crude product. This was further purified by column chromatography using ethyl acetate:hexane (3:7) as a solvent system to obtain the pure product 3 (578 mg, 82% yield).

$^1$H NMR (CDCl$_3$) δ1.20-1.34 (m, 6H), 1.70-2.26 (m, 4H), 2.60-2.80 (m, 4H), 3.14-3.26 (m, 2H), 3.98 (s, 3H), 4.60-4.68 (t, 2H), 4.78 (m, 1H), 4.83 (s, 2H), 6.82 (s, 1H), 7.25-765 (m, 5H), 7.80 (s, 1H), 8.80 (d, J=4.76 1H), 12.20 (s, 1H); FABMS: 706 (M+H).

2S-N-{N1-[4-Chloro-2-(2-chlorobenoyl)phenyl]2-oxy acetamido]-5-methoxy-2-nitrobenzoyl}pyrrolidine-2-carboxaldehyde diethylthioacetal of formula 3 (500 mg, 0.7 mmol) was dissolved in methanol (10 mL), $SnCl_2.2H_2O$ (800 mg, 3.54 mmol) was added and refluxed until the TLC indicated the completion of the reaction. The methanol was then evaporated in vacuum and the aqueous layer was then adjusted to pH 8 with 10% $NaHCO_3$ solution and extracted with ethyl acetate (60 mL). The combined organic phase was dried over $Na_2SO_4$ and evaporated under vacuum to afford the crude amino diethyl thioacetal 4 (460 mg, 96% yield), which was directly used in the next step.

A solution of 2S-N-{N1-[4-chloro-2-(2-chlorobenoyl) phenyl]2-oxy acetamido]-5-methoxy-2-aminobenzoyl}pyrrolidine-2-carboxaldehyde diethylthioacetal 4 (400 mg, 0.7 mmol), $HgCl_2$ (384 mg, 1.42 mmol) and $CaCO_3$ (149 mg, 1.47 mmol) in acetonitrile-water (4:1) was stirred slowly at room temperature for overnight until complete loss of starting material as indicated by the TLC. The clear organic supernatant liquid was extracted with ethyl acetate and washed with saturated 5% $NaHCO_3$ (20 mL), brine (20 mL) and the combined organic phase was dried over $Na_2SO_4$. The organic layer was evaporated in vacuum and to afford a white solid, which was first eluted on a column chromatography with ethyl acetate to remove mercuric salts, and then with ethyl acetate to obtain the pure product 5c (179 mg, 55% yield).

$^1$H NMR ($CDCl_3$) δ1.20-1.35 (m, 6H), 1.7-2.25 (m, 4H), 3.14-3.26 (m, 2H), 3.98 (s, 3H), 4.60-4.68 (m, 1H), 4.78 (s, 1H), 4.83 (s, 2H), 6.82 (s, 1H), 7.25-7.35 (m, 1H), 7.80 (m, 1H), 8.80 (d, 1H, J=4.33 Hz), 12.2 (s, 1H); FABMS: 552 (M+H).

Biological Activity: some of in vitro biological activity studies were carried out at the National Cancer Institute, Maryland, USA.

Cytotoxicity:

The compounds 5a) 7-methoxy-8-{3-[2-benzoyl-(4-chlorophenyloxy)propoxy]}-(11aS)-1,2,3,11a-tetrahydro-5H-pyrrolo[2,1-c][1,4]benzodiazepine-5-one, 5b) 7-metho-xy-8-{4-[2-benzoyl-(4-chlorophenyloxy)butoxy]}-(11aS)-1,2,3,11a-tetrahydro-5H-pyrrolo[2,1-c] [1,4]benzodiazepine-5-one, 5c) 7-methoxy-8-{4-[2-benzoyl-(4,6-dichlorophenyloxy)butoxy]}-(11aS)-1,2,3,11a-tetrahydro-5H-pyrrolo[2,1-c][1,4]benzodiazepine-5-one, 5d) 7-methoxy-8-{6-[2-benzoyl-(4,6-dichloro phenyloxy)hexyloxy]}-(11aS)-1,2,3,11a-tetra-hydro-5H-pyrrolo[2,1-c][1,4]benzodiazepine-5-one, 5e) 7-methoxy-8-{N1-[4-chloro-2-(2-chlorobenzoyl) phenyl]2-oxyacetamido}-(11aS)-1,2,3,11a-tetrahydro-5H-pyrrolo[2,1-c][1,4]benzodiazepine-5-one, were evaluated for in vitro anticancer activity against nine human tumour cells derived from nine cancer types (colon, prostate, oral, lung, cervix and breast cancer) as shown in (Table 1, 2 and 3)

5e was evaluated for in vitro anticancer activity against sixty human tumour cells derived from nine cancer types (leukemia, non-small-cell lung, colon, CNS, melanoma, ovarian, prostate, and breast cancer) as shown in (Table 1 and 2). For the compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The mean graph midpoint values of $\log_{10}$ TGI and $\log_{10}$ LC50 as well as $\log_{10}$ GI50 for 5e is listed in Table 1 and 2). As demonstrated by mean graph pattern, compound 5e exhibited an interesting profile of activity and selectivity for various cell lines. The mean graph mid point of $\log_{10}$ TGI and $\log_{10}$ LC50 showed similar pattern to the $\log_{10}$ GI50 mean graph mid points.

TABLE 1

$\log_{10}$GI50 $\log_{10}$TGI and $\log_{10}$LC50 mean graphs midpoints (MG_MID) of in vitro cytotoxicity data for the representative compounds against human tumour cell lines

| Compound | $\log_{10}$GI50 | $\log_{10}$TGI | $\log_{10}$LC50 |
|---|---|---|---|
| 5f | −6.47 | −5.24 | −4.89 |

TABLE 2

$\log_{10}$LC50 concentration in mol/L causing 50% lethality) values for the representative compound 5e

| Cancer | Compound (5e) |
|---|---|
| Leukemia | −6.26 |
| Non small-cell-lung | −5.44 |
| Colon | −5.67 |
| CNS | −5.23 |
| Melanoma | −5.75 |
| Ovarian | −5.24 |
| Renal | −5.25 |
| Prostate | −4.78 |
| Breast | −5.17 |

Each cancer type represents the average of six to nine different cancer cell lines.

In vitro evaluation of cytotoxic activity. The compound 5a, 5b, 5g, 5i and 5j were evaluated for in vitro anticancer activity against nine human tumour cells derived from six cancer types (colon, prostate, oral, lung, cervix and breast cancer) as shown in Table 3. Compound 5a, 5b and 5g shows promising cytotoxicity against some cancer cell lines (Table 3). Compounds 5a, 5b, 5g, 5i and 5j have been evaluated for their in vitro cytotoxicity in selected human cancer cell lines of colon (Colo205), lung (Hop-62), cervix (SiHa), prostate (DU145, PC3), oral (DWD, HT1080), and breast (MCF7, Zr-75-1) origin. A protocol of 48 h continuous drug exposure has been used and an Adriamycin (ADR) protein assay has been used to estimate cell viability or growth. The results are expressed as percent of cell growth determined relative to that of untreated control cells Compounds 5b, 5g, 5i and 5j exhibited less than 20% cell growth at µg/mL concentration in some cancer cell lines. Compound 5a, Colo205 cell growth by 83%, DU145 cell growth by 84%, DWD cell growth by 70%, Hop62 cell growth by 87%, HT1080 cell growth by 80%, MCF7 cell growth by 73%, PC3 cell growth by 91%, SiHa cell growth by 67%, Zr-75-1 cell growth by 76%. Compound 5b, Colo205 cell growth by 20%, DU145 cell growth by 64%, DWD cell growth by 70%, Hop62 cell growth by 78%, HT1080 cell growth by 72%, MCF7 cell growth by 69%, PC3 cell growth by 72%, SiHa cell growth by 20%, Zr-75-1 cell growth by 20%. Compound 5g, Colo205 cell growth by 50%, DU145 cell growth by 20%, DWD cell growth by 94%, Hop62 cell growth by 84%, HT1080 cell growth by 94%, MCF7 cell growth by 71%, PC3 cell growth by 86%, SiHa cell growth by 74%, Zr-75-1 cell growth by 72%. Compound 5i, DU145 cell growth by 42%, Hop62 cell growth by 60%, HT1080 cell growth by 70%, Compound 5j, Colo205 cell growth by 44%, DU145 cell growth by 57%, DWD cell growth by 65%, Hop62 cell growth by 53%, HT1080 cell growth by 71%, PC3 cell growth by 81%, SiHa cell growth by 77%.

TABLE 3

The percentage cell growth data for representative benzophenone-PBD

| | | | | | Activity status in terms of IC$_{50}$ value (μg/mL) | | | | |
|---|---|---|---|---|---|---|---|---|---|
| Compd. | Colo205 Colon | DU145 Prostate | DWD Oral | Hop62 Lung | HT1080 Oral | MCF7 Breast | PC3 Prostate | SiHa Cervix | Zr-75-1 Breast |
| 5a | 17 | 16 | 30 | 13 | 20 | 27 | 9 | 43 | 24 |
| 5b | 32 | 35 | 30 | 22 | 28 | 31 | 28 | >80 | >80 |
| 5g | 50 | 80 | 6 | 16 | 6 | 29 | 14 | 26 | 28 |
| 5i | >80 | 58 | >80 | 40 | 30 | >80 | >80 | >80 | >80 |
| 5j | 56 | 43 | 35 | 47 | 29 | 68 | 19 | 23 | >80 |
| ADR | 5 | 6 | 2 | 5 | 4 | 5 | 5 | 5 | 5 | hybrids
ADR = Adiramycin is the control drug

Thermal Denaturation Studies

Compounds were subjected to thermal denaturation studies with duplex-form calf thymus DNA (CT-DNA) using an adaptation of a reported procedure. Working solutions in aqueous buffer (10 mM NaH$_2$PO$_4$/Na$_2$HPO$_4$, 1 mM Na$_2$EDTA, pH 7.00+0.01) containing CT-DNA (100 μm in phosphate) and the PBD (20 μm) were prepared by addition of concentrated PBD solutions in DMSO to obtain a fixed [PBD]/[DNA] molar ratio of 1:5. The DNA-PBD solutions were incubated at 37° C. for 0, 18, and 36 h prior to analysis. Samples were monitored at 260 nm using a Beckman DU-7400 spectrophotometer fitted with high performance temperature controller, and heating was applied at 1° C. min−1 in the 40-90° C. range. DNA helix coil transition temperatures (Tm) were obtained from the maxima in the (dA260)/dT derivative plots. Results are given as the mean ±standard deviation from three determinations and are corrected for the effects of DMSO co-solvent using a linear correction term. Drug-induced alterations in DNA melting behaviour are given by: ΔTm=Tm(DNA+PBD)−Tm (DNA alone), where the Tm value for the PBD-free CT-DNA is 69.0±0.01. The fixed [PBD]/[DNA] ratio used did not result in binding saturation of the host DNA duplex for any compound examined. Compound 5a, 5b, 5g 5i and 5j at 0 hr, 18 hr and 36 hr gradually increased at 37° C.

TABLE 4

Thermal denaturation data of C8-linked benzophenone hybrids of pyrrolo[2,1-c]-[1,4]benzodiazepine with calf thymus (CT) DNA

| | | ΔT$_m$ (° C.)$^a$ after incubation at 37° C. for | | |
|---|---|---|---|---|
| Compd. | [PBD]:[DNA] molar ratio$^b$ | 0 h | 18 h | 36 h |
| 5a | 1:5 | 1.4 | 1.7 | 2.2 |
| 5b | 1:5 | 1.5 | 2.1 | 2.6 |
| 5g | 1:5 | 1.4 | 1.6 | 2.3 |
| 5i | 1:5 | 1.5 | 1.9 | 2.6 |
| 5j | 1:5 | 1.8 | 2.0 | 2.8 |
| DC-81 | 1:5 | 0.3 | 0.7 | |

$^a$For CT-DNA alone at pH 7.00 ± 0.01, T$_m$ = 69.6° C. ± 0.01 (mean value from 10 separate determinations), all ΔT$_m$ values are ±0.1-0.2° C.
$^b$For a 1:5 molar ratio of [ligand]/[DNA], where CT-DNA concentration = 100 μM and ligand concentration = 20 μM in aqueous sodium phosphate buffer [10 mM sodium phosphate + 1 mM EDTA, pH 7.00 ± 0.01].

ADVANTAGES OF THE INVENTION

1. The present invention provides a new pyrrolo[2,1-c][1,4]benzodiazepine hybrids useful as antitumour agents.
2. It also provides a process for the preparation of novel pyrrolo[2,1-c][1,4]benzodiazepine hybrids.

What is claimed is:
1. A compound having formula 5

Formula 5 wherein:
n is an integer having the value between 1and 5;
each of $X^1$, $X^2$, and $X^3$ is independently selected from the group consisting of H, Cl, and $CH_3$;
Y is selected from the group consisting of O and NH; and
Z is selected from the group consisting of C=O and $CH_2$.
2. The compound according to claim 1, wherein the compound is selected from the group consisting of:
7-methoxy-8-{3-[2-benzoyl-(4-chlorophenyloxy)propoxy]}-(11aS)-1,2,3,11a-tetra hydro-5H-pyrrolo[2,1-c][1,4]benzodiazepine-5-one(5a);
7-methoxy-8-{4-[2-benzoyl-(4-chlorophenyloxy)butoxy]}-(11aS)-1,2,3,11a-tetrahydro-5H-pyrrolo[2,1-c][1,4]benzodiazepine-5-one(5b);
7-methoxy-8-{5-[2-benzoyl-(4chlorophenyloxy)pentoxy]}-(11aS)-1,2,3,11a-tetrahydro-5H-pyrrolo[2,1-c][1,4]benzodiazepine-5-one(5c);
7-methoxy-8-{3-[2-benzoyl-(4-chloro-6-methylphenyloxy)propoxy]}-(11aS)-1,2,3,11a-tetrahydro-5H-pyrrolo[2,1-c][1,4]benzodiazepine-5-one(5d);
7-methoxy-8-{3-[2-benzoyl-(4-chloro-6-methylphenyloxy)butoxy]}-(11aS)-,2,3,11a-tetra hydro-5H-pyrrolo[2,1-c][1,4]benzodiazepine-5-one (5e);
7-methoxy-8-{3-[2-benzoyl-(4-chloro-6-methylphenyloxy)pentoxy]}-(11aS)-1,2,3,11a-tetra hydro-5H-pyrrolo[2,1-c][1,4]benzodiazepine-5-one(5f);
7-methoxy-8-{3 -[2-benzoyl-(4,6- dichlorophenyloxy)propoxy]}-(11aS)-1,2,3,11a-tetra hydro-5H-pyrrolo[2,1-c][1,4]benzodiazepine-5-one (5g);
7-methoxy-8-{3 -[2-benzoyl-(4,6-dichlorophenyloxy)butoxy]}-(11aS)-1,2,3,11a-tetrahydro-5H-pyrrolo[2,1-c][1,4]benzodiazepine-5-one (5h);

7-methoxy-8-{3-[2-benzoyl-(4,6-di-chlorophenyloxy) hexyloxy]}-(11aS)-1,2,3,11a-tetra hydro-5H-pyrrolo [2,1-c][1,4]benzodiazepine-5-one (5i);

7-Methoxy-8-{N1-[4-chloro-2-(2-chlorobenzoyl)phenyl] 2-oxyacetamido }-(11aS)-1,2,3,11a-tetrahydro-5H-pyrrolo[2,1-c][1,4]benzodiazepine-5-one (5j);

7-Methoxy-8-{N1-[4-chloro-2-(2-chlorobenzoyl)phenyl] 2-oxypropinamido}-(11aS)-1,2,3,11a-tetrahydro-5H-pyrrolo[2,1-c][1,4]benzodiazepine-5-one (5k); and 7-Methoxy-8-{N1-[4-chloro-2-(2-chlorobenzoyl)phenyl] 2-oxybutanamido}-(11aS)-1,2,3,11a-tetrahydro-5H-pyrrolo[2,1-c][1,4]benzodiazepine-5-one (5l).

3. The compound according to claim 1, wherein compound is selected from the group consisting of compounds of Formulae 5a-c, 5d-f, 5g-i, and 5 j-l, wherein in compounds of Formulae 5a-c, 5d-f, and 5 j-l, n is an integer independently having the value between 1 and 3, and in compounds of Formulae 5g-i, n is an integer independently having the value between 1 and 4:

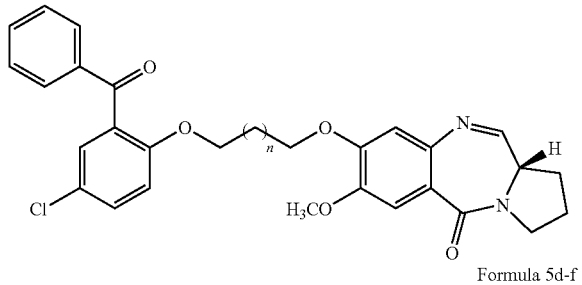

Formula 5a-c

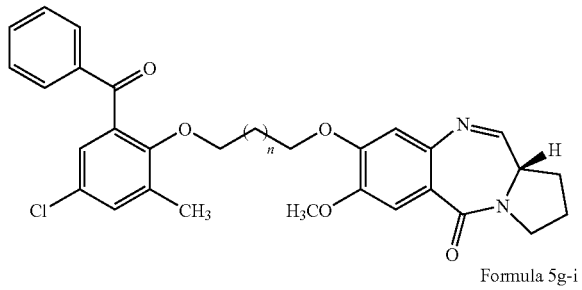

Formula 5d-f

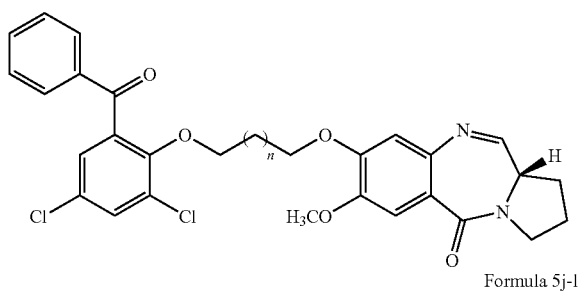

Formula 5g-i

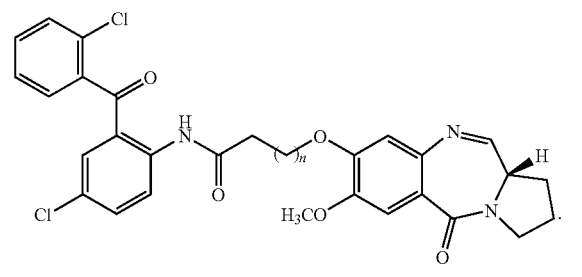

Formula 5j-l

4. A pharmaceutical composition comprising at least one compound of claim 1 or derivatives, analogues, or salts thereof, and optionally pharmaceutically acceptable carriers, adjuvants and additives.

5. The pharmaceutical composition according to claim 4, wherein in the compound of formula 5, the value of n is between 1 and 4.

6. A process for the preparation of a compound of formula 5,

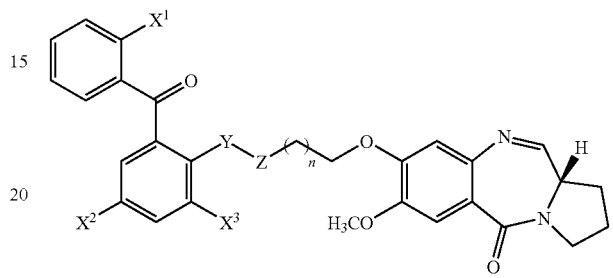

Formula 5 wherein:
n is an integer having the value between 1 and 4;
each of $X^1$, $X^2$, and $X^3$ is independently selected from the group consisting of H, Cl, and $CH^3$;
Y is selected from the group consisting of O and NH; and
Z is selected from the group consisting of C=O and $CH^2$, the process comprising the steps of:

a) reacting(2)-N-(4-hydroxy-3-methoxy-2-nitrobenzoyl) pyrrolidine-2-carbox aldehyde diethylthioacetal of formula 2

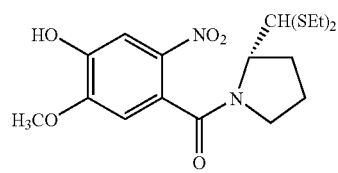

2 with [2-(n-bromoalkyl)-n-chlorophenyl)(phenyl) methanone or acetamide of formula 1

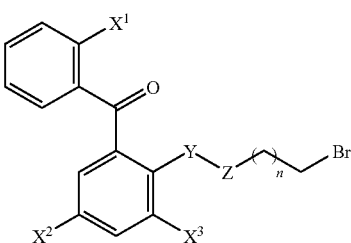

1 wherein each of $X^1$, $X^2$ and $X^3$ is independently selected from the group consisting of H, Cl and $CH_3$; Y is selected from the group consisting of O and NH; Z is selected from the group consisting of C=O and $CH_2$; n=1 to 4, in an aprotic water miscible organic solvent, in the presence of an anhydrous mild inorganic base, under refluxing temperature in an oil bath, for a period of about 48 hrs, followed by the removal of the inorganic base by filtration and evaporating the organic solvent to obtain the resultant crude product and purifying it to obtain the desired product of (2S)-N-{n benzoyl(phenyloxy)alkoxy/[(n benzoyl)phenyl]2-oxyacetamido]5-methoxy-2-nitrobenzoyl}-pyrrolidine-2-carboxaldehyde diethylthioacetal of formula 3,

3

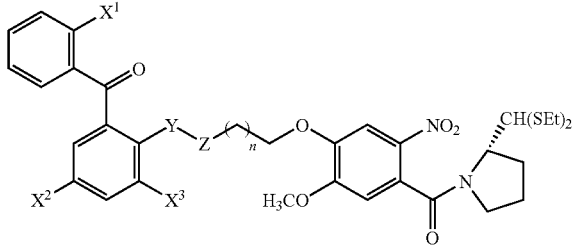

wherein each of $X^1$, $X^2$ and $X^3$ independently selected from the group consisting of H, Cl and $CH^3$; Y is selected from the group consisting of O and NH; Z is selected from the group consisting of C=O and $CH^2$; n=1 to 4, b) reducing (2S)-N-{n benzoyl(phenyloxy)alkoxy/(n benzoyl)phenyl]2-oxy acetamido]-5-methoxy-2-nitrobenzoyl}-pyrrolidine-2-carboxaldehyde diethylthioacetal of formula 3 with anhydrous tin chloride, in an alcohol, under reflux, followed by the evaporation of the alcohol and adjusting the pH of the resultant product layer to about 8 by using a base, followed by extraction with ethyl acetate and washing the combined organic phase with a brine solution and evaporating the solvent to obtain the desired (2S)-N-{n benzoyl (phenyloxy) alkoxy/[(n-benzoyl)phenyl]2-oxyacetamido]-5-methoxy-2-amino benzoyl}-pyrrolidine-2-carboxaldehyde diethylthioacetal of formula 4,

4

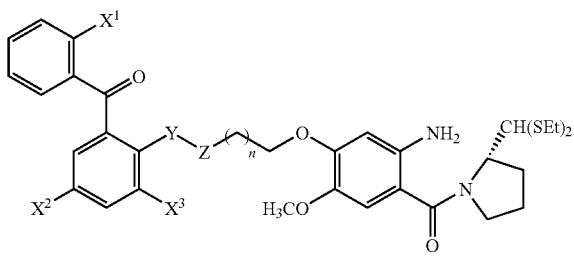

wherein each of $X^1$, $X^2$ and $X^3$ is independently selected from the group consisting of H, Cl and $CH_3$; Y is selected from the group consisting of O and NH; Z is selected from the group consisting of C=O and $CH_2$; n=1 to 4 and c) reacting(2S)-N-{n-benzoyl(phenyloxy)alkoxy/[(n-benzoyl)phenyl]-2-oxy acetamido]-5-methoxy-2-aminobenzoyl}-pyrrolidine-2-carboxaldehyde diethylthioacetal of formula 4 with mercurous chloride, in a mixture of water and an organic solvent, in the presence of mild inorganic, under stirring, at a temperature of about 20-30° C., for a period of 8-12 hrs, followed by the extraction of yellow organic supernatant and washing with sodium bicarbonate and brine, respectively, and evaporating the organic layer, under reduced pressure to obtain the compound of formula 5 thereby.

7. The process according to claim 6, wherein the mild inorganic base used in steps (a) and (b) is calcium carbonate.

8. The process according to claim 6, wherein the aprotic water miscible organic solvent used in step (a) is selected from the group consisting of acetone and acetonitrile.

9. The process according to claim 6, wherein the organic solvent used in step (c) is selected from the group consisting of acetonitrile and acetone.

10. The process according to claim 6, wherein the alcohol used in step (b) is selected from the group consisting of methanol and ethanol.

11. The process according to claim 6, wherein the compound of formula 5 is selected from the group consisting of:
7-methoxy-8-{3-[2-benzoyl-(4-chlorophenyloxy)propoxy]}-(11aS)-1,2,3,11a-tetra hydro-5H-pyrrolo[2,1-c][1,4]benzodiazepine-5-one (5a);
7-methoxy-8-{4-[2-benzoyl-(4-chlorophenyloxy) butoxy]}-(11aS)-1,2,3,11a-tetrahydro-5H-pyrrolo[2,1-c][1,4]benzodiazepine-5-one (5b);
7-methoxy-8-{5-[2-benzoyl-(4chlorophenyloxy) pentoxy]}-(11aS)-1,2,3,11a-tetrahydro-5H-pyrrolo[2,1-c][1,4]benzodiazepine-5-one (5c);
7-methoxy-8-{3-[2-benzoyl-(4-chloro-6-methylphenyloxy)propoxy]}-(11aS)-1,2,3,11a-tetrahydro-5H-pyrrolo[2,1-c][1,4]benzodiazepine-5 -one (5d);
7-methoxy-8-{3-[2-benzoyl-(4-chloro-6-methylphenyloxy)butoxy]}-(11aS)-1,2,3,11a-tetra hydro-5H-pyrrolo[2,1-c][1,4]benzodiazepine-5-one (5e);
7-methoxy-8-{3-[2-benzoyl-(4-chloro-6-methylphenyloxy)pentoxy]}-(11aS)-1,2,3,11a-tetra hydro-5H-pyrrolo[2,1-c][1,4]benzodiazepine-5-one (5f);
7-methoxy-8-{3-[2-benzoyl-(4,6-dichlorophenyloxy)propoxy]}-(11aS)-1,2,3,11a-tetra hydro-5H-pyrrolo[2,1-c][1,4]benzodiazepine-5-one (5g);
7-methoxy-8-{3-[2-benzoyl-(4,6-dichlorophenyloxy)butoxy]}-(11aS)-1,2,3,11a-tetra hydro-5H-pyrrolo[2,1-c][1,4]benzodiazepine-5-one (5h);
7-methoxy-8-{3-[2-benzoyl-(4,6-di-chlorophenyloxy) hexyloxy]}-(11aS)-1,2,3,11a-tetrahydro-5H-pyrrolo[2,1-c][1,4]benzodiazepine-5-one (5i);
7-Methoxy-8-{N1-[4-chloro-2-(2-chlorobenzoyl)phenyl] 2-oxyacetamido }-(11aS)-1,2,3,11a-tetrahydro-5H-pyrrolo[2,1-c][1,4]benzodiazepine-5-one (5j);
7-Methoxy-8-{N1-[4-chloro-2-(2-chlorobenzoyl)phenyl] 2-oxypropinamido}-(11aS)-1,2,3,11a-tetrahydro-5H-pyrrolo[2,1-c][1,4]benzodiazepine-5-one (5k); and
7-Methoxy-8 -{N1-[4-chloro-2-(2-chlorobenzoyl)phenyl] 2-oxybutanamido}-(11aS)-1,2,3,11a-tetrahydro-5H-pyrrolo[2,1-c][1,4]Benzodiazepine-5-one (5ll).

* * * * *